US009004805B2

(12) United States Patent
Changsrivong et al.

(10) Patent No.: US 9,004,805 B2
(45) Date of Patent: Apr. 14, 2015

(54) MULTI-STAGE ENGAGEMENT ASSEMBLIES AND RELATED METHODS

(75) Inventors: Derek Changsrivong, Foothill Ranch, CA (US); Hugh Cook, Foothill Ranch, CA (US)

(73) Assignee: BAL Seal Engineering, Inc., Foothill Ranch, CA (US)

(*) Notice: Subject to any disclaimer, the term of this patent is extended or adjusted under 35 U.S.C. 154(b) by 189 days.

(21) Appl. No.: 13/304,004

(22) Filed: Nov. 23, 2011
(Under 37 CFR 1.47)

(65) Prior Publication Data
US 2012/0134742 A1    May 31, 2012

Related U.S. Application Data

(60) Provisional application No. 61/430,912, filed on Jan. 7, 2011, provisional application No. 61/418,331, filed on Nov. 30, 2010.

(51) Int. Cl.
| F16B 21/00 | (2006.01) |
| F16B 7/04 | (2006.01) |
| A61F 2/78 | (2006.01) |
| F16B 21/18 | (2006.01) |
| F16B 21/20 | (2006.01) |

(52) U.S. Cl.
CPC ........... *F16B 7/0406* (2013.01); *Y10T 403/604* (2015.01); *Y10T 29/49826* (2015.01); *Y10T 403/602* (2015.01); *Y10T 403/581* (2015.01); *Y10T 403/553* (2015.01); *A61F 2/78* (2013.01); *A61F 2002/7887* (2013.01); *F16B 21/18* (2013.01); *F16B 21/183* (2013.01); *F16B 21/186* (2013.01); *F16B 21/205* (2013.01)

(58) Field of Classification Search
CPC ........................................... F16B 21/18
USPC ............. 403/294, 315–319, 327, 328, 359.5, 403/360; 29/896.92
See application file for complete search history.

(56) References Cited

U.S. PATENT DOCUMENTS

| 1,332,291 A | * | 3/1920 | Goodell ......................... 292/327 |
| 5,161,838 A | * | 11/1992 | Ely et al. ......................... 292/327 |
| 5,545,842 A | * | 8/1996 | Balsells ......................... 174/372 |
| 5,938,474 A | * | 8/1999 | Nelson .......................... 439/583 |

(Continued)

FOREIGN PATENT DOCUMENTS

| FR | 2 390 618 | 12/1978 |
| WO | WO 2008/100319 A1 | 8/2008 |

OTHER PUBLICATIONS

Extended European Search Report from corresponding European Application No. 11190981.8 (10 pages).

*Primary Examiner* — Daniel P Stodola
*Assistant Examiner* — Jonathan Masinick
(74) *Attorney, Agent, or Firm* — Klein, O'Neill & Singh, LLP

(57) ABSTRACT

A progressive release or multi-point engagement device according to aspect of the present disclosure includes a first component and a second component connected to the first component with mounted coil spring. The first component is movable relative to the second component and latch by moving the canted coil spring to a second common groove. Alternatively, a second spring is used to move the second component and relative to a third component. When a second engagement position is desired, a relatively higher a force may be necessary to move the relevant component.

12 Claims, 7 Drawing Sheets

(56) References Cited

U.S. PATENT DOCUMENTS

| | | | |
|---|---|---|---|
| 5,956,871 A * | 9/1999 | Korsen | 36/134 |
| 6,406,074 B1 * | 6/2002 | Mahaney | 292/327 |
| 6,749,358 B2 * | 6/2004 | Balsells | 403/316 |
| 7,175,441 B2 * | 2/2007 | Naviaux et al. | 439/8 |
| 2006/0228166 A1 * | 10/2006 | Balsells | 403/57 |
| 2009/0149053 A1 | 6/2009 | Chansrivong | |
| 2010/0029145 A1 * | 2/2010 | Balsells et al. | 439/827 |

* cited by examiner

MULTI-STAGE ENGAGEMENT ASSEMBLIES AND RELATED METHODS

CROSS-REFERENCE TO RELATED APPLICATION

This is a regular utility application of provisional application No. 61/430,912, filed Jan. 7, 2011, and of provisional application No. 61/418,331, filed Nov. 30, 2010, the contents of each of which are expressly incorporated herein by reference.

FIELD OF ART

The present application generally relates to devices with multi-stage latch, lock or hold mechanisms with specific discussions extended to assemblies with two or more latch, lock or hold points within each assembly to provide multiple latching, locking, and/or holding.

BACKGROUND

In certain applications where components within a device are mechanically connected, the joint or device connecting the components may be designed to disconnect or fail in order to prevent damage to the device. An example of such an application is the connection between prosthesis and a metallic bone graft by which the prosthesis is anchored to a user's body. In the event that high external forces are applied to the prosthesis, the biomechanical joint between the prosthesis and the bone may be damaged. Accordingly, all or portions of the prosthesis are typically designed to disconnect from the body in order to prevent damage to the biomechanical joint and/or the bone to which the prosthesis is connected. Other examples or applications include breakaway car parts, housing covers for electronic devices, toys, amusement park rides, aerospace parts or devices, etc.

Certain application may require two objects to move relative to each other and be able to connect to each other with multiple alternative connecting forces depending on the position of one object relative to the other object. In certain other applications where objects within a device are mechanically connected, the connection between the objects may be designed to disconnect or fail in order to prevent damage to the device. Examples of the applications discussed above include the connection between prosthesis and a metallic bone graft by which the prosthesis is anchored to a user's body, breakaway car parts, housing covers for electronic devices, toys, amusement park rides, aerospace parts or devices, etc.

SUMMARY

A progressive release device according to aspect of the present disclosure includes a first component, a second component connected to the first component with a first canted coil spring, and a third component connected to the second component with a second canted coil spring. A force required to release the connection between the second component and the third component is less than a force required to release the connection between the first component and the second component.

In an example, the first canted coil spring is captured by a groove located on the second component and a groove located on the first component.

In an example, the second canted coil spring is captured by a groove located on the second component and a groove located on the third component.

In an example, the second component is located inside the first component.

In an example, the third component is slidable relative to the second component and the first component.

In an example, the third component is made from at least two separate parts that are attached to one another.

According to other aspects of the disclosure, the progressive release device can be used in a device for supplementing or replacing a part of a body, such as a prosthetic limb. The device for supplementing or replacing a part of a body includes a first part configured to connect to the body at a biomechanical joint, and a second part configured to function as the part of the body. The first component of the progressive release device is connected to the first part, and the third component is connected to the second part. The progressive release device at least partially disconnects the first part and the second part at a first force level to warn a user of possible impending damage to the part of the body. The progressive release device then completely disconnects the first part and the second part at a second force level greater than the first force level to prevent damage to the part of the body.

A method of assembling the progressive release device includes releasably connecting a first component to a second component with a first canted coil spring, the connection being releasable with a first force exerted on at least one of the first component or the second component. The method also includes releasably connecting the second component to a third component with a second canted coil spring, the connection being releasable with a second force exerted on at least one of the second component or the third component. The second force is less than the first force.

A method of making a device with multi-stage engagement, the method comprising releasably connecting a first component to a second component with a first canted coil spring, the connection being releasable with a first force exerted on at least one of the first component or the second component; releasably connecting the second component to a third component with a second canted coil spring, the connection being releasable with a second force exerted on at least one of the second component or the third component; wherein the second force is less than the first force.

In an example, the method further comprising latching the first component to the second component by providing a common groove that captures the first canted coil spring and deflecting a minor axis of the first canted coil spring when applying an axial force on the first component or the second component.

In an example, the method further comprising latching the second component to the third component by providing a common groove that captures the second canted coil spring and deflecting a minor axis of the second canted coil spring when applying an axial force on the second component or the third component.

In an example, the method further comprising locking the second component to the third component by providing a common groove that captures the second canted coil spring and loading the second canted coil spring along its major axis.

In an example, the method further comprising sliding the third component relative to the second component.

In an example, the method further comprising placing the second component inside the first component.

According to aspects of the disclosure, a multi-stage latch device includes a shaft, a housing having a bore configured to receive the shaft, at least two grooves in the bore of the housing or on the shaft, and at least one canted coil spring configured to be housed in any one of the grooves to provide multiple latching connections between the housing and the shaft.

According to additional aspects of the disclosure, a method of latching two parts includes inserting the first part into a bore of the second part, the first part or the second part including at least two grooves configured to receive a caned coil spring, moving the first part in the bore to latch the first part to the second part in a first latched position, wherein the canted coil spring is located in one of the grooves, and moving the first part in the bore to latch the first part to the second part in a second latching position, wherein the canted coil spring is located in the other groove.

A device with multi-stage engagement comprising a shaft; a housing having a bore configured to receive the shaft; a first groove and a second groove in the bore of the housing or on the shaft; and a canted coil spring positionable in the first groove when a first axial force is applied on the shaft or on the housing and in the second groove when a second axial force is applied on the shaft or on the housing, the second axial force being higher than the first axial force.

In an example, the device further comprising a retaining groove for retaining the canted coil spring before assembly of the shaft into the bore of the housing.

In an example, a sidewall of the second groove has a greater taper relative to a centerline of the shaft than a sidewall of the first groove.

In an example, a bottom wall of the first groove and a bottom wall of the second groove have different depths relative to a centerline of the shaft.

In an example, the shaft is connected to a first article of manufacture.

In an example, a bottom wall of the second groove is at least 1.5 times longer than a bottom wall of the first groove.

The various embodiments of the present progressive release device have several features, no single one of which is solely responsible for its desirable attributes. Without limiting the scope of the present embodiments as expressed by the claims that follow, the more prominent features of the progressive release device will now will be discussed briefly. After considering this discussion, and particularly after reading the section entitled "Detailed Description" one will understand how the features of the present embodiments provide advantages in various applications.

BRIEF DESCRIPTION OF THE DRAWINGS

The various embodiments of the present connectors, systems, and associated methods now will be discussed in detail with an emphasis on highlighting the advantageous features. These embodiments depict the novel and non-obvious connectors shown in the accompanying drawings, which are for illustrative purposes only. These drawings include the following figures, in which like numerals indicate like parts.

DETAILED DESCRIPTION

The embodiments of the present connectors, systems, and associated methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unit or a unitary piece and whereas a unitary piece means a singularly formed single piece, such as a singularly formed mold or cast. Still further, the terms "first" and "second" used herein are understood as identifiers only to distinguish between different components. Thus, unless the context indicates otherwise, "first" and "second" are not limiting terms and merely refer to two different components.

Figure 1:
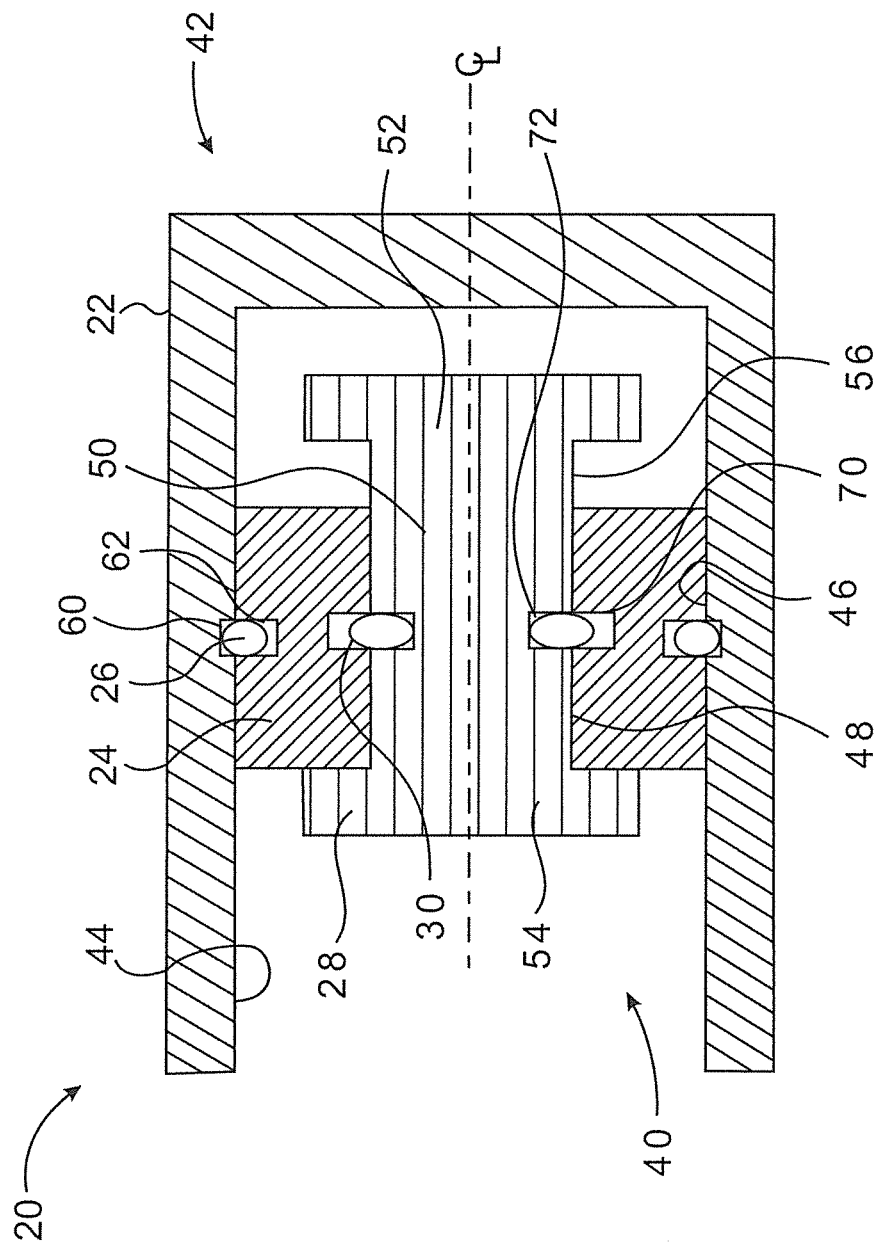
FIG. 1 shows a simplified cross-sectional view of a progressive release device in accordance with an embodiment.

FIG. 1 illustrates a device 20 according to one embodiment of the present device, system, and method. The device may be referred to as a progressive release device or a multi-stage latching, locking or holding device 20 and includes a first component 22 and a second component 24 that can be configured with a hold, latched or locked connection with each other by a first canted coil spring 26. As described in detail below, when the first component 22 and the second component 24 are in a latched or a locked connection, the canted coil spring 26 is engaged in at least one common groove located in the first component 22 and the second component 24. When the first component 22 and the second component 24 are in a hold connection, the canted coil spring 26 is engaged in at least one groove located in either the first component 22 or the second component 24. The device may be referred to as a device with multi-stage engagement, which can be holding, latching, locking, or combinations thereof. The progressive release device 20 further includes a third component 28 that is in a latched or locked connection with the second component 24 by a second canted coil spring 30. As described in detail below, when the third component 28 and the second component 24 are in a latched or a locked connection, the canted coil spring 30 is engaged in at least one common groove located in the second component 24 and the third component 28. When the third component 28 and the second component 24 are in a hold connection, the canted coil spring 30 is engaged in at least one groove located in either the third component 28 or the second component 24. The connection between the second component 24 and the third component 28 may be understood to be the first connection. The connection between the first component 22 and the second component 24 may be understood to be the second connection.

In the following, the first connection and the second connection are described as latched connections with the understanding that either of these connections may be a holding or a locking connection depending on functional and performance requirements or preferences of the progressive release device in a particular application. As described in detail below, releasing the first connection requires less force than a force required to release or disconnect the second connection.

Accordingly, when a progressively increasing force is applied to the first component 22 and/or the third component 28, the first connection is disconnected before the second connection. As used herein, latching is understood to include capturing a spring between two grooves, i.e. a common groove, but permit unlatching while locking is understood to include capturing a spring between two grooves but does not permit unlatching unless the spring is destroyed.

Figure 2A:
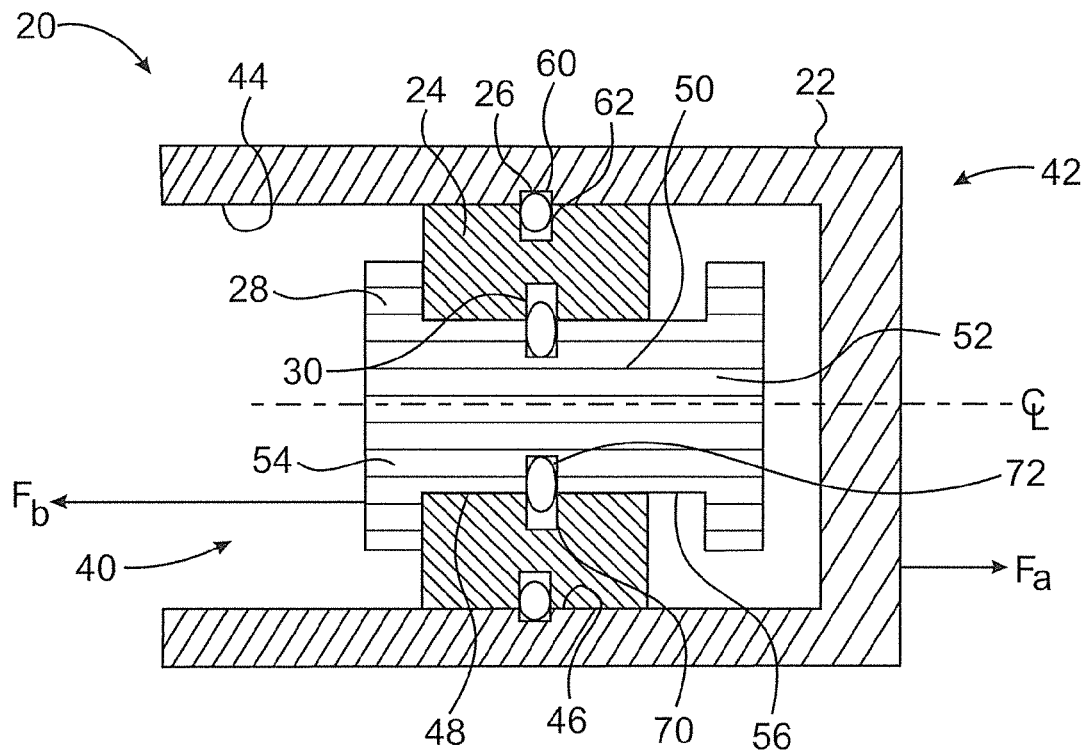
FIGS. 2A-3B show the progressive release device of FIG. 1 used in a biomechanical prosthesis.
Figure 2B:
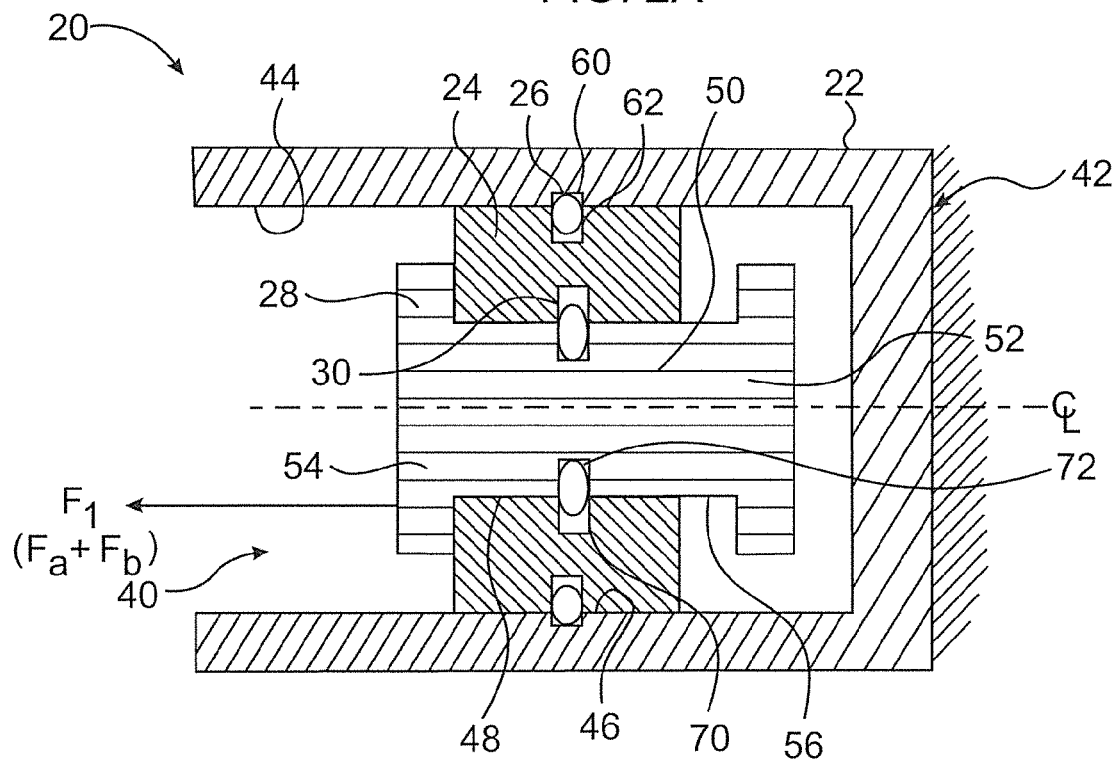

With reference to FIG. 2A, the first component may be connected to an external device (not shown), which may exert a force Fa on the first component 22 along a centerline ℄. The force Fa tends to move the first component 22 in the direction of the force Fa along the centerline. The third component 28 may be connected to the same or another external device (not shown), which may exert a force Fb of equal, less or greater than force Fa on the third component 28 along the centerline ℄. The force Fb tends to move the third component 28 along the centerline ℄. The forces Fa and Fb oppose each other by being directed outward along the centerline ℄. Accordingly, the forces Fa and Fb tend to pull apart the third component 28 and the first component 22. In this scenario, both the first connection and the second connection experience a net force F1 that is equal to the sum of the magnitudes of the forces Fa and Fb along the centerline ℄. As shown in FIG. 2B, this net force F1 can be resolved as a single force exerted on the third component 28 with the assumption that the first component 22 is fixed.

Figure 3A:
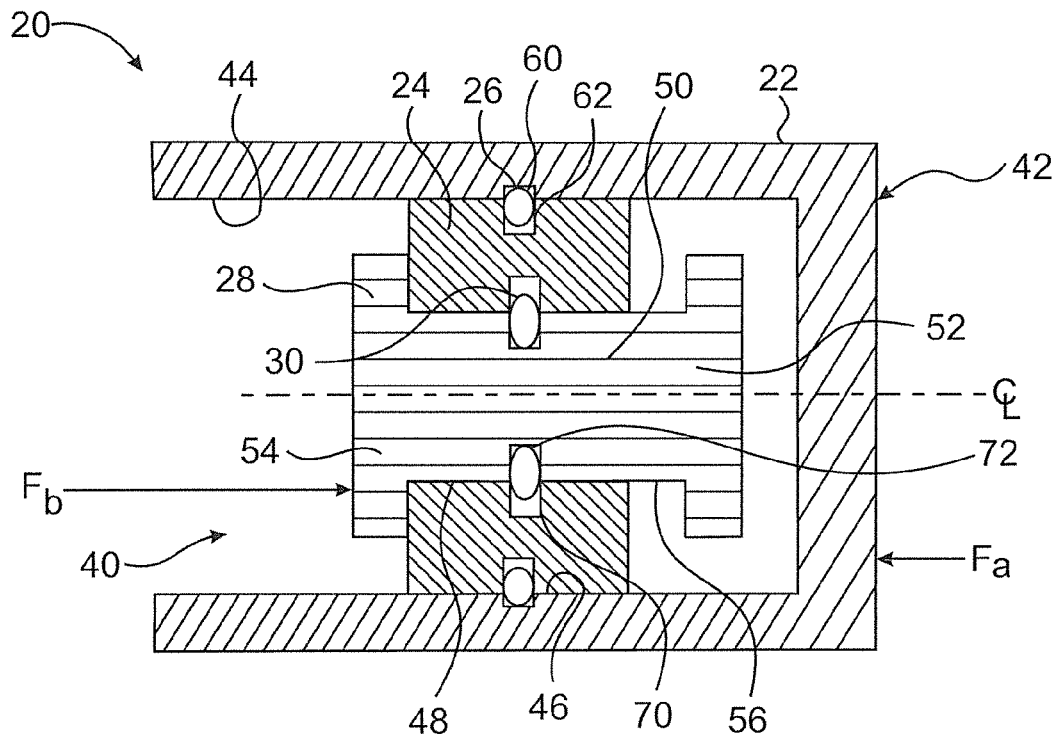
Figure 3B:
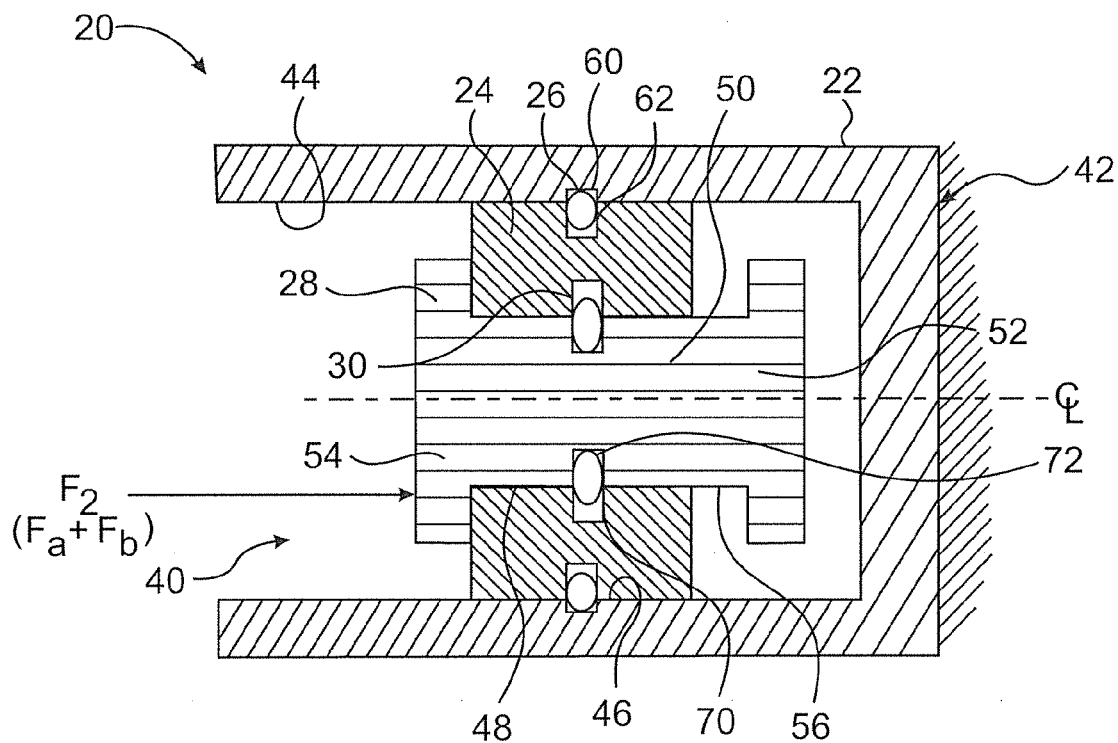

With reference to FIG. 3A, the forces Fa and Fb are shown opposed each other by being directed toward each other along the centerline ℄. Accordingly, the forces Fa and Fb tend to push the third component 28 and the first component 22 together. In this scenario, both the first connection and the second connection experience a net force F2 that is equal to the sum of the magnitudes of the forces Fa and Fb along the centerline ℄. As shown in FIG. 3B, this net force F2 can be resolved as a single force exerted on the third component 28 with the assumption that the first component 22 is fixed. If the forces Fa and Fb are in the same direction along the centerline ℄, then the resulting net force is the difference in magnitude between the forces Fa and Fb with the direction of the net force being the some as the direction of the greater force of the forces Fa and Fb. Therefore, for the purpose of describing the effect of various forces exerted on the first connection and/or the second connection of the progressive release device 20, a net force F that is oriented generally along the centerline ℄ and exerted on the third component 28 is described herein with the assumption that the first component 22 is fixed. One of ordinary skill in the art will readily recognize that a number of different forces exerted on the first component 22, the second component 24 and/or the third component 28 can be resolved into a single net component force F exerted on the third component 28 along the centerline ℄ with the assumption that the first component 22 is fixed.

In the embodiment of FIG. 1, the first component 22 is a sleeve having an open end 40, a closed end 42 and an inner wall 44. The first component 22 may have any cross-sectional shape, such as circular, oval, square, complex, or rectangular. Additionally, both ends 40 and 42 of the first component 22 may be open, have shoulders, a tapered section, etc. The second component 24 is a collar having an outer wall 46 and a through bore defining an inner wall 48. The cross-sectional shape of the outer wall 46 is similar to the cross-sectional shape of the inner wall 44 of the first component 22 within some acceptable tolerance to permit relative movement between the two. Additionally, the dimensions of the outer wall 46 relative to the centerline ℄ are slightly less than the corresponding dimensions of the inner wall 44 relative to the centerline ℄. For example, if the inner wall 44 is cylindrical, then the outer diameter of the outer wall 46 is slightly less than the inner diameter of the inner wall 44. Accordingly, the second component 24 can be inserted in the first component 22 and move therein along the centerline ℄. In other embodiments, additional components such as collars and couplings may be incorporated to provide a progressive release device with more than two latch or lock locations.

The third component 28 has a first section 50 and two end sections 52 and 54. One or both end sections 52, 54 may be separately formed and subsequently attached to the first section 50 to facilitate assembly. Alternatively or in addition thereto, the second component 24 may be made from two or more parts that are assembled together to couple with the third component 28. The cross-sectional shape of an outer wall 56 of the first section 50 is similar to cross-sectional shape of the inner wall 48 of the second component 24 within some acceptable tolerance to permit relative movement between the two. For example, the dimensions of the outer wall 56 relative to the centerline ℄ are slightly less than the corresponding dimensions of the inner wall 48 of the second component 24 relative to the centerline ℄. If the cross section of the inner wall 48 is circular, then the outer diameter of the outer wall 56 is slightly smaller than the inner diameter of the inner wall 48. Accordingly, the third component 28 can be inserted in the second component 24 and move therein along the centerline ℄. In some embodiments, lubricants or bearings may be used to facilitate movement. For example, Teflon sleeve bearings may be incorporated.

The first section 50 of the third component 28 has an axial length that is greater than the axial length of the second component 24. Furthermore, each of the end sections 52 and 54 has a larger outer diameter than the diameter of the inner wall 48. i.e. the bore. Accordingly, the first section 50 is movable within the bore defined by the inner wall 48 until one of the end sections 52 or 54 abuts a corresponding end surface of the second component 24. Thus, the end sections 52 and 54 function as stops during movement of the third component 28 relative to the second component 24. In other embodiments, the third component 28 may include only one end section 54 to prevent the third component 28 from being completely removed from the second component 24. In such embodiments, the closed end 42 of the first component 22 engages the third component 28 to function as a stop for limiting the movement of the first section 50 of the third component 28. In some embodiments, bumpers or cushions may be incorporated to soften any impact that may occur during relative movements between the various components.

In the embodiments shown in FIGS. 1-4, the second connection between the first and second components 22, 24 is a latching connection. To provide a latching connection, the first component 22 and the second component 24 have a common circumferential groove for receiving the spring 26. The common groove is defined by a groove 60 in the inner wall 44 of the first component 22 configured to receive a portion of the spring 26 and a groove 62 in the outer wall 46 of the second component 24 configured to receive another portion of the spring 26. In the embodiment of FIG. 1, the spring 26 is an axial canted coil spring. In other embodiments, a radial canted coil spring may be used with tapered grooves to direct the loading force of the radial canted coil spring in a desired direction. When the spring 26 is inside the grooves 60 and 62, it engages the walls of the grooves 60 and 62 in a compressed state to latch the second component 24 to the first component 22. The latching strength of the second connection depends, at least in part, on the shapes of the grooves 60 and 62, the spring itself, or both. For example, the spring spacing, the canted angle, the wire diameter used to form the spring, and the material type may be adjusted to provide the spring with a desired holding, latching, and/or locking strength. The grooves 60 and 62 may be annular or may extend less than the entire circumference of the first component 22 and the second component 24. For example, the grooves 60 and 62 may extend partially around the first component 22 and the second component 24, respectively. The grooves can have various groove geometries, including a flat bottom wall, a tapered bottom wall, a complex bottom wall with two or more tapered surfaces, tapered side walls or straight, i.e., non-tapered, side walls. Groove geometries can affect the force necessary to unlatch by rotating the spring axis to a certain orientation to require a higher or a lower force to deflect the spring during unlatching.

In the embodiments shown in FIGS. 1-4, the first connection is a latching connection. To provide a latching connection, the third component 28 and the second component 24 have a common circumferential groove for receiving the spring 30. The common groove is defined by a groove 70 in the inner wall 48 of the second component 24 configured to receive a portion of the spring 30 and a groove 72 in the outer wall 56 of the first section 50 of the third component 28 configured to receive another portion the spring 30. In the embodiment of FIG. 1, the spring 30 is an axial canted coil spring. When the spring 30 is inside the grooves 70 and 72, it engages the walls of the grooves 70 and 72 in a compressed state to latch the second component 24 to the third component 28. The latching strength of the second connection depends at least in part on the shapes of the grooves 70 and 72, the spring type, or both. The grooves 70 and 72 may not extend the entire circumference of the second component 24 and the third component 28. The grooves 70 and 72 may be annular or may extend only partially around the second component 24 and the third component 28, respectively.

Referring to FIGS. 2B and 3B, the grooves and the springs can also be configured such that the magnitude of the force F1 is more than, less than or substantially equal to the magnitude of the force F2. For example, a particular application of the progressive release device 20 may require the force F1, which can be considered as the force required to pull apart the third component 28 from the second component 24 to be greater than the force F2, which can be considered as the force required to push apart the third component 28 from the second component 24. In such an application, the grooves 70 and 72 can be shaped to allow easier pulling apart (shown in FIG. 2B) than pushing apart (shown in FIG. 3B) of the third component 28 from the second component 24. Alternatively, the springs for the two common grooves may be sized to separate at different forces while keeping the two grooves the same. In yet another alternative embodiment, the grooves are structured to have different groove configurations while keeping the springs the same. In yet another embodiment, the grooves and the springs may differ between the first connection and the second connection.

As discussed above, the type of connection between two parts, such as a latching connection or a locking connection, depends at least upon the shape of the groove in each part. For example, a groove having tapered or inclined sidewalls can provide a latching connection because the taper in each sidewall can lift the spring to gradually compress as the spring is guided out of the common groove. A groove having a rectangular shape, such as a flat bottom wall or a tapered bottom wall located between one or two vertical sidewalls (i.e., perpendicular to the centerline), can provide a locking connection. The vertical sidewalls may not lift the spring to compress it and therefore prevent the spring from being removed from the common groove without destroying the spring. However, in the locking configuration, a sufficiently high separation force can distort or damage the spring to enable separation between the first component and the second component, or between the second component and the third component. Accordingly, a latching connection can be reusable while a locking connection may not be reusable unless the spring is replaced. Furthermore, the taper or inclination of the sidewalls of the groove is at least one factor in the strength of the latching connection. Thus, a groove with highly inclined sidewalls will provide a higher strength latching connection as compared to a groove having slightly (relatively less) inclined sidewalls. The higher inclined sidewalls require higher disconnect force to separate the first component from the second component, or the second component from the third component. Additional information regarding connect and disconnect forces and inclined load and release angles is disclosed in Publication No. 2010/0028076 A1 the contents of which are expressly incorporated herein by reference.

In a holding connection, typically only one of the components incorporates a groove for receiving a canted coil spring. Accordingly, when the two parts are connected, a portion of the spring is positioned in the groove of one part while another portion of the spring is compressed against an outer surface of other part. The frictional contact between the spring and the outer surface of the part, which does not have a groove, provides a holding connection. Accordingly, a holding connection provides a generally weaker connection, e.g., lower force to disconnect, than a latching connection, which generally provides a weaker connection than a locking connection, assuming, for example, the same spring is used for all three configurations. In the embodiments of FIGS. 1-4, the first connection and the second connection are shown to be based upon a common groove between the connected parts to define a latched connection or a locked connection. However, the first connection and/or the second connection can also be holding connections, which use a single groove but not a common groove. One of ordinary skill in the art will readily appreciate that each of the first connection or the second connection can be configured as holding, latching or locking connection depending on the strength of the connection that is preferred for a particular application of the progressive release device. Further detail regarding connection of two components with a canted coil spring and the effect of groove shape and spring characteristics on the resulting type of connection is provided in U.S. Pat. Nos. 4,678,210; 5,082,390; 5,411,348; 5,545,842; 6,749,358; 6,835,084; 7,070,455; and 7,195,523, the contents of all of which are expressly incorporated herein by reference.

Figure 4:
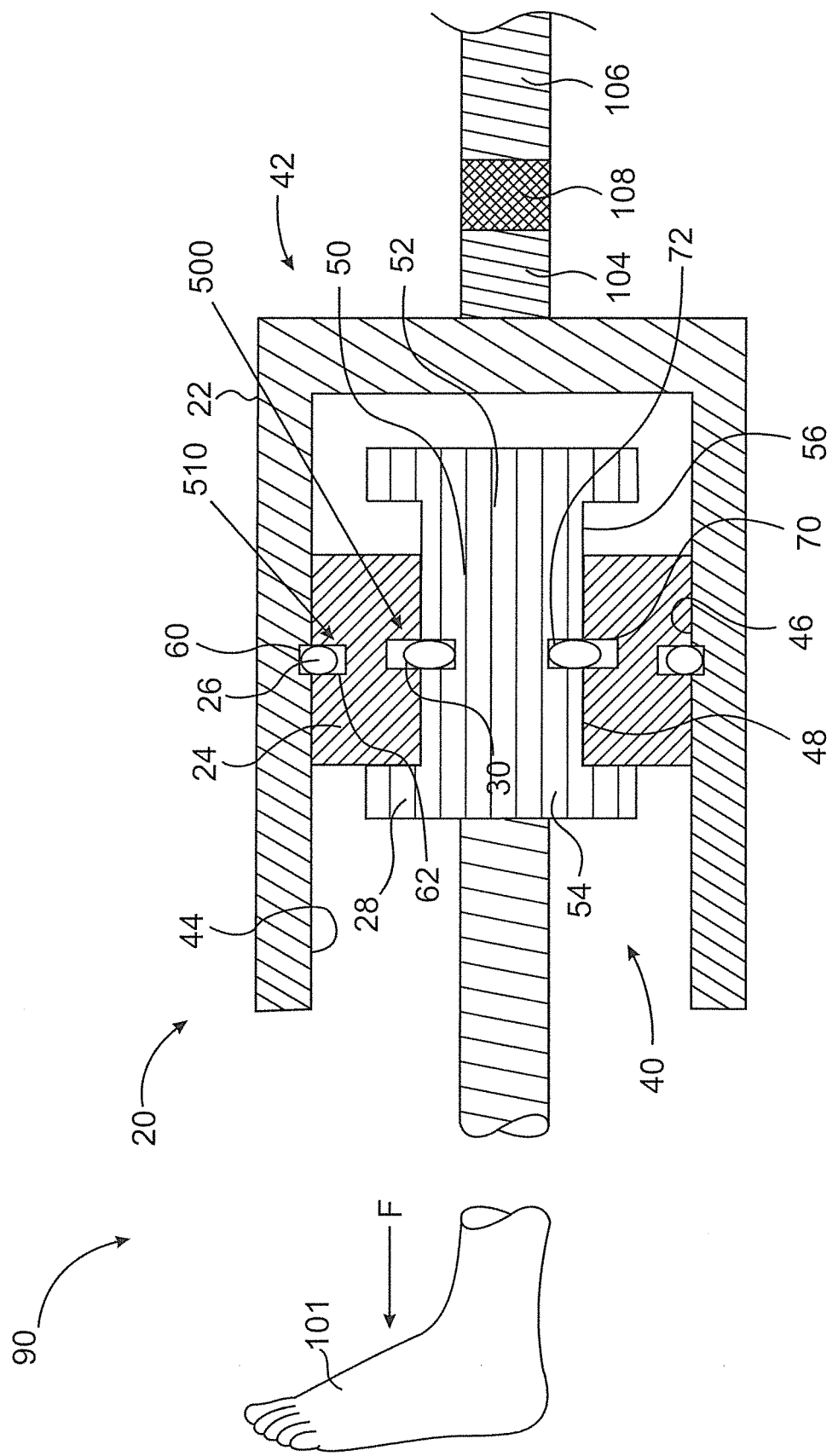
FIG. 4 shows a progressive release device in accordance with an embodiment used in a prosthetic leg.

FIG. 4 shows an exemplary application of the progressive release device 20. The progressive release device 20 can be used to connect a prosthetic limb 90 to a human or an animal body part through a biomechanical joint. The user of the prosthetic limb 90 is referred to herein as the "user." The prosthetic limb 90 may be an artificial leg, foot, hand, arm or any other artificial structure that replaces a portion of a limb, supplements the functions of a limb, or connects a bone to an external device. En the example of FIG. 4, the prosthetic limb 90 is a prosthetic leg and may be referred to as prosthetic leg 90. The prosthetic leg 90 includes a main member, a leg joint, a shaft or a first lower extremity 100, which is configured to function as a replacement for an amputated leg of the user. The main member 100 may be connected to an articulating or a fixed artificial foot 101. The prosthetic leg 90 also includes a base member, upper leg join, upper shaft, or a second extremity 104 that is connected to or is integral with one end of a biomechanical joint 102. The opposite end of the biomechanical joint 102 is connected to or is integral with the user's body 106, such as the upper thigh bone, knee, or hip. The biomechanical joint 102 may be formed by a bone graft structure 108. The bone graft structure 108 may include a mesh or a lattice having therein bone material such as bone graft, bone cement and/or other materials that are typically used for connecting fractured bone and/or promoting, bone growth. The mesh provides structural support and further promotes bone growth. The above-described biomechanical joint 102 is only one example of various devices, systems and methods that can be used for connecting or fusing an artificial member to a biological member such as a bone or living tissue. One of ordinary skill in the art will recognize that numerous other devices, systems and methods can be used for this purpose.

The progressive device 20 connects the main member 100 with the base member 104. As shown in FIG. 4, the main member 100 is connected to the third component 28, and the base member 104 is connected to the first component 22. The base member 104 generates forces in various directions due to the movement of the bone 106, which may be the result of the user's movements. For example, any walking or jumping by the user exerts forces on the base member 104. The artificial foot 101 also exerts forces on the main member 100. For example, the user's walking or jumping generates impact forces on the artificial foot 101 that are transferred to the main member 100. In another example the user utilizing the artificial foot 101 for stability and/or leverage when lifting objects or exercising exerts forces on the main member 100.

The biomechanical joint 102 experiences all of the above-described forces because it connects the bone 106 to the artificial leg 90. As described in detail below, in order to prevent injury to the bone 106 and/or damage to the biomechanical joint 102, the progressive release device 20 provides two levels of protection for the biomechanical joint 102 and/or the bone 106. The progressive release device 20 initially provides a warning to the user if the force exerted on the biomechanical joint 102 is near the force required to damage/injure the biomechanical joint 102 or the bone 106. This warning entails disconnecting the first connection when the net force F exerted on the third component 28 exceeds a first predetermined force level. If the activity continues, the progressive release device 20 has additional means for preventing damage/injury to the user, such as to the biomechanical joint 102 or the bone 106. In the embodiment shown, the device is configured to disconnect the second connection if the force exerted on the third component 28 exceeds a second predetermined force level that is greater than the first predetermined force level, but less than the force required to damage the biomechanical joint 102 and/or the bone 106. Note that the first, second, and third components 22, 24, 28 may be sized and structured in any number of configurations to permit the desired separation, gap, room or space for relative movement upon disconnection of the first connection and the second connection. Thus, in the embodiment of FIG. 4, a gap may be provided between the end section 54 of the third component 28 and the end edge of the second component 24 to permit separation of the of the first connection. The progressive release device, having at least two latching points, may be referred to as a multi-latching device that serially latches depending on the exerted force.

Referring to FIG. 4, a force F is shown being exerted on the main member 100. The force F may be generated by impact between the prosthetic leg 90 and an object during walking or jumping. The force F is transferred to the third component 28 through the main member 100. The third component 28 then transfers the force to the first component 22 through spring 30, the second component 24 and spring 26. A force F2 required to disconnect the first connection 500 is less than the force F1 required to disconnect the second connection 510. In addition, the force F2 is less than a force F3 required to damage the biomechanical joint 102 and/or injure the bone 106. When the force F reaches F1, the first connection 500 is disconnected, but the second component 24 remains intact because F1<F2. The third component 28 is now freely movable within the second component 24. The end sections 52 and 54 prevent the third component 28 from being completely removed from the second component 24. The free movement of the third component 28 to the extent allowed by the stops 52 and 54 serves as a warning to the user to stop the activity which caused the disconnection of the first connection 500 and reconnect the third component 28 to the second component 24. In the event that either the user ignores the disconnection of the first connection or the force F abruptly increases to F2 without the user's control, the second connection 510 is disconnected in order to prevent damage/injury to the biomechanical joint 102. After the disconnection of the first connection, the second connection, or both, the prosthetic leg 90 is no longer functional and the user must reestablish the first and/or second connections in order to use the prosthetic leg 90.

As described above, the progressive device 20 can connect two parts to each other and provide a first release or disconnect mechanism that serves as a warning indicating that the two parts may become completely disconnected if the forces on the progressive device 20 are increased. Additionally, the progressive device 20 includes a second release or disconnect mechanism for completely disconnecting the parts in order to prevent damage to any of the two parts due to excessive forces exerted on one or both of the parts. In another embodiment, audible alarm or signal may be incorporated to further alert the user of the potential risks of excessive force, such as upon separation of either the first connection and/or the second connection.

Figure 5A:
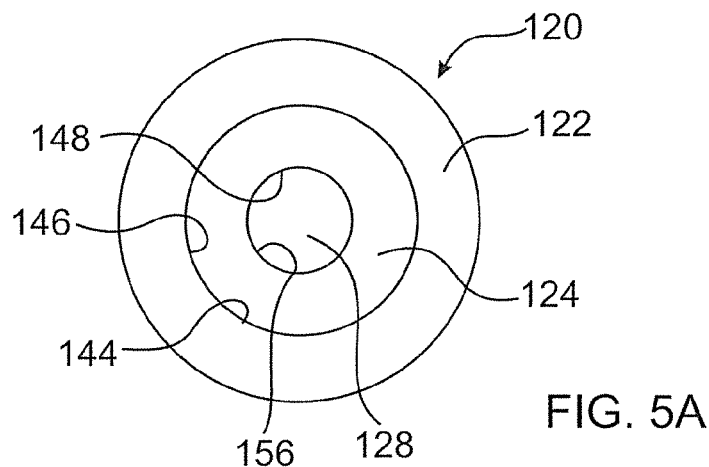
FIGS. 5A-5C show a progressive release device in accordance other embodiments.
Figure 5B:
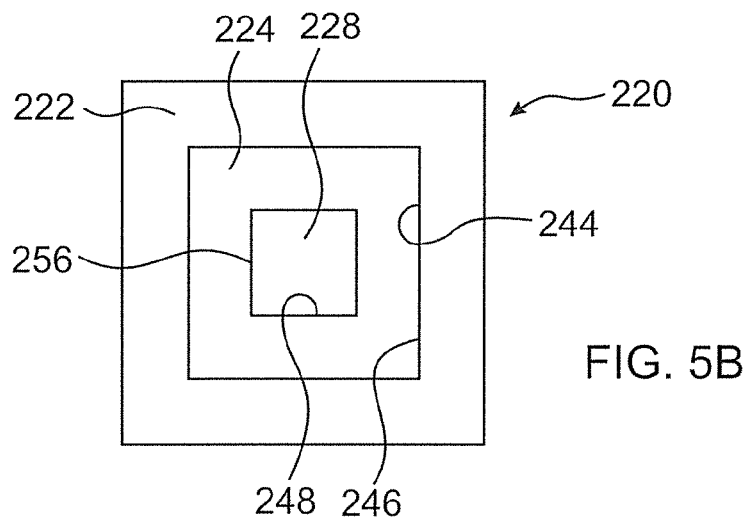
Figure 5C:
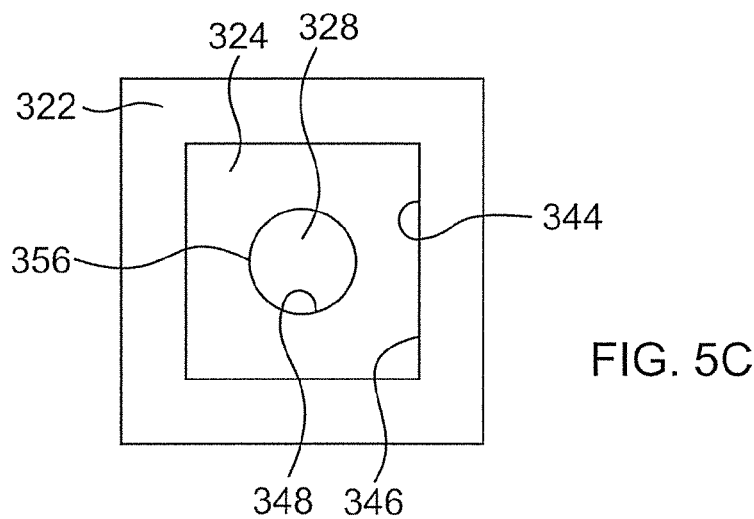

The first component 22, the second component 24 and the third component 28 can have any cross sectional shape to provide a particular function for the progressive release device 20. For example, FIGS. 5A-5C illustrate exemplary progressive release devices 120, 220 and 320, respectively, according to other embodiments. In the embodiment of FIG. 5A, the progressive release device 120 has a first component 122, a second component 124 and a third component 128, all of which have circular cross sections. In particular, the inner wall 144 of the first component 122 and the outer wall 146 of the second component 124 have circular cross sections. Accordingly, these two components are rotatable relative to each other, which may be preferred in a particular application. Similarly, the inner wall 148 of the second component 124 and the outer wall 156 of the third component 128 have circular cross sections. Accordingly, these two components are rotatable relative to each other, which may be preferred in a particular application.

In the embodiment of FIG. 5B, the progressive release device 220 has a first component 222, a second component 224 and a third component 228, all of which have square cross sections. In particular, the inner wall 244 of the first component 222 and the outer wall 246 of the second component 224 have square cross sections. Accordingly, these two components are not rotatable relative to each other, which may be preferred in a particular application. Similarly, the inner wall 248 of the second component 224 and the outer wall 256 of the third component 228 have square sections. Accordingly, these two components are not rotatable relative to each other, which may be preferred in a particular application. For example, in the prosthetic leg 90 described above, the progressive device 220 may be preferred because rotation of the prosthetic leg 90 should be exclusively controlled by the user. Accordingly, the progressive release device 220 may be suitable for use in the prosthetic leg 90.

In the embodiment of FIG. 5C, the progressive release device 320 has a first component 322, a second component 324 and a third component 328. The inner wall 344 of the first component 322 and the outer wall 346 of the second component 324 have square cross sections. Accordingly, these two components are not rotatable relative to each other, which may be preferred in a particular application. However, the inner wall 348 of the second component 324 and the outer wall 356 of the third component 328 have circular cross sections. Accordingly, these two components may be rotatable relative to each other, which may be preferred in a particular application.

The exemplary progressive devices described herein have three nested components, namely the first component, the second component, which is movable within the first component, and the third component, which is movable within the second component. In accordance with other embodiments, a progressive release device can have any number of nested components in order to provide a number of preferred functions in a particular application, such as four or more nested components. Each nested component can be held, latched or locked within an adjacent outer component and require a release force that may be the same or different from the release forces required for the release of the other components from each other.

As understood from the present disclosure, the progress release device with at least three or more nested components may be used in a number of different applications, such as in aerospace, energy distribution, consumer electronics, automotive, medical device, house ware, toys, and other industries to progressively control connect and disconnect forces between the nested components. The progressive release device may be used not only as a warning device as discussed herein, but also as feedback and indicator using two distinct connect/disconnect forces. Thus, again with reference to FIG. 4, instead an artificial limb, the main member 100 and the base member 104 may be structures or objects that are usable in consumer or industrial products. For example, the main member 100 and the base member 104 may be part of a gym equipment and the progressive release device 90 is configure to separate to prevent injuries. As another non-limiting example, the main member 100 and the base member 104 may be part of a load bearing structure, such as a shelf, and the progressive release device 90 is configured to separate to warn the user of over loading.

Figure 6:
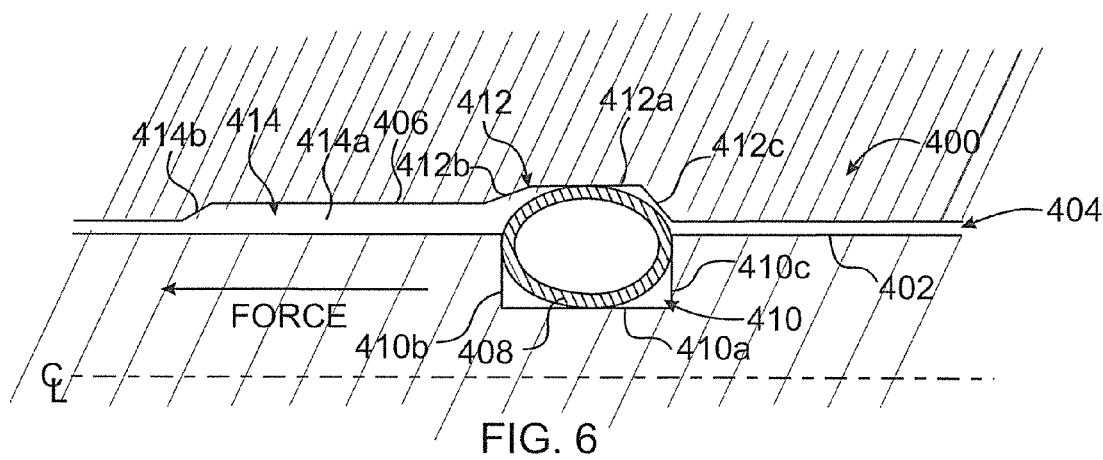
FIG. 6 is a side cross-sectional view of a latch device according to another embodiment.

Referring to FIG. 6, a multi-stage latching device 400 according to one exemplary embodiment is shown. The latch device 400 comprises a shaft 402 being inserted into a bore 404 of a housing 406 along a centerline ℄ to engage the housing 406 with at least one canted coil spring 408. The shaft 402 is inserted into the bore 404 by applying a force in the direction shown by the arrow in FIG. 6. The shaft 402 may have any cross-sectional shape, such as cylindrical, rectangular, triangular, oval, etc. The shaft 402 includes at least one annular groove 410, which in the exemplary embodiment of FIG. 6 is shown to have a rectangular shape. The groove 410 includes a bottom 410a, which is flat in the direction of the centerline ℄ (as viewed in cross section in FIG. 6), and two side walls 410b and 410c. The spring 408 is a canted coil spring, which, in this embodiment, is a radial canted coil spring with an axial canted coil spring contemplated with corresponding changes to the grooves. The spring 408 is positioned in the groove 410 before the shaft 402 is inserted into the housing 406. The housing 406 includes at least an annular first groove 412 and an annular second groove 414. The first groove 412 has a bottom, wall or surface 412a, which is flat in the direction of the centerline ℄ (as viewed in cross section in FIG. 6) and two sidewalls 412b and 412c that are inclined toward the centerline ℄. The first groove 412 transitions into the second groove 414 with the inclined sidewall 412b. The second groove 414 includes a bottom 414a, which is flat in the direction of the centerline ℄ (as viewed in cross section in FIG. 6). The second groove 414 also includes an inclined sidewall 414b spaced from the sidewall 412b of the first groove 412. In other embodiments, the groove 410 on the shaft and the grooves 412, 414 on the housing are reversed so that the housing has a single groove while the shaft has the two grooves.

When the shaft 402 is inserted into the bore 404 of the housing 406, the canted coil spring 408 is compressed by the inner walls of the bore 404 until the spring 408 reaches the first groove 412. The spring 408 then slightly expands so as to engage the first groove 412 while still compressed by the bottom wall surfaces 410a, 412a of the two grooves 412, 410. This position represents a first latched position between the shaft 402 and the housing 404, which is shown in FIG. 6. If the shaft 402 is further inserted into the bore 404 by a force in the direction shown, the sidewall 412b engages or abuts the spring 408 and compresses the spring 408 radially, along the minor axis of the spring, i.e. the smaller axis. The degree of inclination of the sidewall 412b can affect the amount of force required for further insertion of the shaft 402 into the bore 404. As the shaft 402 is further inserted into the bore 404 from the first latched position, the sidewall 412b compresses the spring 408 until the spring 408 engages the bottom 414a of the second groove 414 and is located in the groove 414. This position represents a second latched position between the shaft 402 and the housing 404 (not shown). Because the depth of the second groove 414 is less than the depth of the first groove 412, the spring 408 is in a more compressed state in the second latched position as compared to the first latched position. Therefore, the second latched position provides a higher latching force than the first latched position, especially if the groove gap between the two bottom surfaces 410a, 414a is configured to operate to the right of a typical flat or constant load range of a canted coil spring. The latch device 400 can be used in applications that require multiple latching connections with different latching forces. For example, in another embodiment (not shown), a third groove is provided in the housing 406. In yet another embodiment, more than three grooves are provided in the housing 406. In still yet another example, the latch device 400 may be used with a prosthetic foot shown in FIG. 4. As an alternative, as discussed above, the latch device 400 may be used in a gym equipment to soften impact or in a load bearing application.

Thus, as shown and described, the second groove 414 is understood to incorporate a bottom surface 414a having a length that is at least 1.5 times longer than the bottom surface 412a of the first groove 412. In a particular embodiment, the length is about 1.6 times to about 3.5 times the length of the bottom surface 412a of the first groove. However, depending on a location of a second latching or locking position, the length can be longer than 3.5 times. Moreover, the second groove 414 is configured no that the spring 408 is compressed by the bottom surface 414a of the first groove and permitted to slide along a length of the bottom surface 414a until it contacts a sidewall 414b of the second groove. In the embodiment shown, the bottom surface 414a of the second groove has a constant diameter between the second inclined surface 414b and the first inclined surface 412b.

Figure 7:
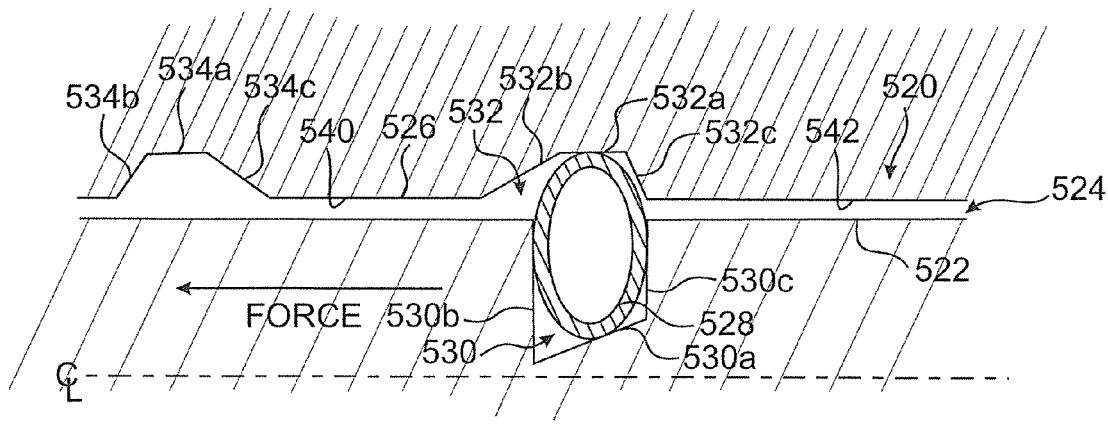
FIG. 7 is side cross-sectional view of a latch device according to another embodiment.

Referring to FIG. 7, a multi-stage latching device 520 according to another exemplary embodiment is shown. The latch device 520 is formed by a shaft 522 being inserted into a bore 524 of a housing 526 along a centerline ℄ to engage the housing 526 with at least one canted coil spring 528. The shaft 522 is inserted into the bore 524 by applying a force in the direction shown by the arrow in FIG. 7. The shaft 522 may have any cross-sectional shape, such as cylindrical, rectangular, triangular, oval, etc. The shaft 522 includes at least one annular groove 530, which in the exemplary embodiment of FIG. 7 is shown to have a trapezoidal shape. For example, the groove 530 includes a bottom wall or surface 530a and is inclined relative to the centerline ℄. The groove 530 includes two side walls 530b and 530c. As shown, the two side walls 530b, 530c are straight or non-tapered relative to a perpendicular line with the centerline ℄ and are generally parallel to one another. The spring 528 is a canted coil spring, which can be an axial canted coil spring in this embodiment. The spring 528 is positioned in the groove 530 before the shaft 522 is inserted in the housing 526. The housing includes at least an annular first groove 532 and an annular second groove 534. The first groove 532 has a bottom wall 532a, which is flat in the direction of the centerline ℄ (as viewed in cross section in FIG. 7) and two sidewalls 532b and 532c that are inclined toward the centerline ℄. The second groove 534 includes a bottom wall 534a, which is flat in the direction of the centerline ℄ (as viewed in cross section in FIG. 7) and two sidewalls 534b and 534c that are inclined toward the centerline ℄. The two grooves 532, 534, and more particularly the two inclined surfaces 532b, 534c of the two grooves 532, 534 are separated from one another by an interior dividing wall surface 540 of the housing 526.

When the shaft 522 is inserted into the bore 524 of the housing 526, the canted coil spring 528 is compressed by the inner walls 542 of the bore 524 until the spring 528 reaches the groove 532. The spring 528 then slightly expands so as to engage the groove 532 while still compressed by the bottom walls 532a, 530a of the two grooves 530, 532. This position represents a first latched position between the shaft 522 and the housing 524, which is shown in FIG. 7. If the shaft 522 is further inserted into the bore 524 in the direction of the arrow, the sidewall 532b of the first groove 532 engages or abuts the spring 528 and compresses the spring 528. The degree of inclination of the sidewall 532b and of the bottom wall 530a of the shaft groove can affect the amount of force required for further insertion of the shaft 522 into the bore 524. As the shaft 522 is further inserted into the bore 524 from the first latched position, the sidewall 532b followed by the interior dividing wall 540 of the bore 524 compress the spring 528 and turn the spring clockwise until the spring 528 reaches the second groove 534. The spring 528 then slightly expands and rotates counter-clockwise to engage the groove 534 while still remain axially compressed. This position represents a second latched position between the shaft 522 and the housing 524 (not shown).

The sidewall 534b is shown to have a more steep inclination than the sidewall 532b of the first groove. Accordingly, unlatching the shaft 522 from the first latched position by moving the shaft 522 deeper into the bore 534 requires less force than unlatching the shaft 522 from the second latch position by moving the shaft 522 farther out of the bore 524, further in the direction of the arrow. Therefore, the second latching position provides a greater latching force than the first latched position to move the shaft along the direction of the arrow. One of ordinary skill in the art will readily recognize that the depth of the grooves 532 and 534, the inclination of the sidewalls 532b, 534c and the inclination of the bottom walls 530a. 532a can determine the relative latching forces provided in the first latched position and the second latched position. The groove configurations further determine the forces required to move the shaft 524 in the bore 524 between the two latched positions. The latch device 520 can be used in applications that require multiple latching connections with different latching forces, such as for a prosthetic device as described with reference to FIG. 4.

Thus, aspects of the present device, system, and method include a latching device comprising two grooves each having a bottom wall surface separated from one another by an interior dividing wall 540, which has a smaller wall diameter than the wall diameter of the first bottom wall 532a, the second bottom wall 534a, or both the first and the second bottom walls. In another embodiment, the first groove has a tapered side wall 532b that is less inclined than a corresponding tapered side wall 534b of the second groove so that separation of the spring from the first groove requires less force than separation of the spring from the second groove, in the same separation direction.

Figure 8:
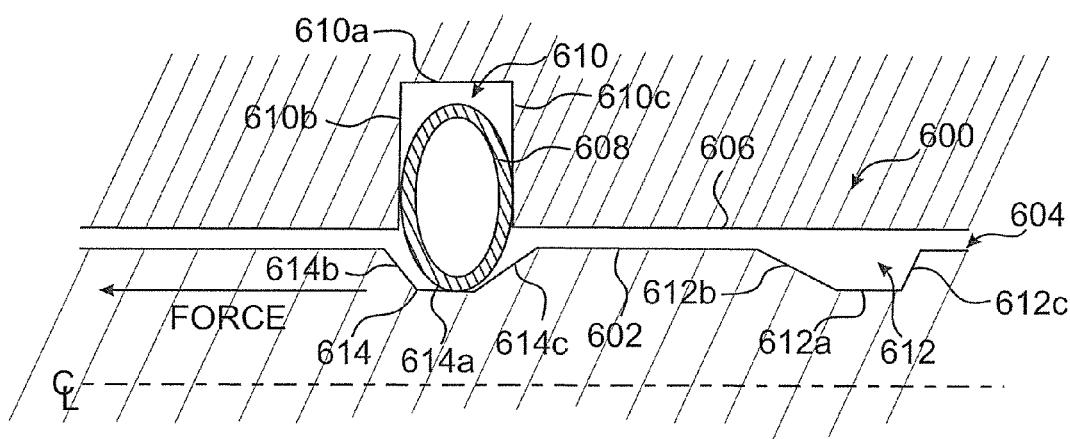
FIG. 8 is side cross-sectional view of a latch device according to another embodiment.

Referring to FIG. 8, a latch device 600 according to another exemplary embodiment is shown, which has a multi-stage latching mechanism. The latch device 600 is formed by a shaft 602 being inserted into a bore 604 of a housing 606 along a centerline ℄ to engage the housing 606 with at least one canted coil spring 608. The shaft 602 is inserted into the bore 604 by applying a force in the direction shown by the arrow in FIG. 8. The shaft 602 may have any cross-sectional shape, such as cylindrical, rectangular, triangular, oval, etc. The housing 602 includes at least one annular groove 610, which in the exemplary embodiment of FIG. 3, is shown to have a rectangular shape or square shape. Accordingly, the groove 610 includes a bottom wall 610a, which is flat along the direction of the centerline ℄ (as viewed in cross section in FIG. 8) and two sidewalls 610b and 610c that are perpendicular to the bottom wall. The spring 608 is a canted coil spring, which in the preset embodiment can be an axial garter canted coil spring. The spring 608 is positioned in the groove 610 of the housing 606 before the shaft 602 is inserted in the housing 606. The shaft 604 includes at least an annular first groove 614 and an annular second groove 612. The first groove 614 includes a flat bottom surface 614a in the direction of the centerline ℄ (as viewed in cross section in FIG. 7) and two sidewalls 614b and 614c that are inclined away from the centerline ℄. The second groove 612 has a flat bottom surface 612a in the direction of the centerline ℄ (as viewed in cross section in FIG. 8) and two sidewalls 612b and 612c that are inclined away from the centerline ℄.

When the shaft 602 is inserted into the bore 604 of the housing 606, the canted coil spring 608 expands radially within the housing groove 610 and compresses axially by the shaft 602 until the first groove 614 reaches the spring 608. The spring 608 then compresses radially inwardly so as to engage the first groove 614 while still compressed axially against the two side walls 610c, 610b. This position represents a first latched position (not shown) between the shaft 602 and the housing 606. Note that the spring is spaced from the bottom wall 610 of the housing groove 610 in the first latched position. If the shaft 602 is further inserted into the bore 604, the sidewall 614b engages the spring 608 and compresses the spring 608 both radially and axially. The degree of inclination of the sidewall 614b can affect the amount of force required for further insertion of the shaft 602 into the bore 604. As the shaft 602 is further inserted into the bore 604 from the first latched position, the sidewall 614b followed by the inner wall of the bore 604 compress the spring 608 radially and cause it to expand radially deeper into the housing groove 610 until the spring 608 reaches the second groove 612. The spring 608 then slightly contracts to engage the groove 612 while still compressed axially. This position represents a second latched position between the shaft 602 and the housing 604, which is not shown. Note that the spring is also spaced from the bottom wall 610 of the housing groove 610 in the second latched position (not shown). The sidewall 614c is shown to have a more steep inclination than the sidewall 614c. Accordingly, unlatching the shaft 602 from the first latched position by moving the shaft 602 deeper into the bore 614, i.e., further in the direction of the arrow, requires less force than unlatching the shaft 602 from the second latch position by moving the shaft 602 farther out of the bore 604 and out of the second groove 612. One of ordinary skill in the art will readily recognize that the depth of the grooves 612 and 614 and the inclination of the sidewalls 612c and 614c can determine the relative latching forces provided in the first latched position and the second latched position, and further determine the forces required to move the shaft 602 in the bore 604 between the two latched positions. The latching device 600 can be used in applications that require multiple latching connections with different latching forces.

Figure 9:
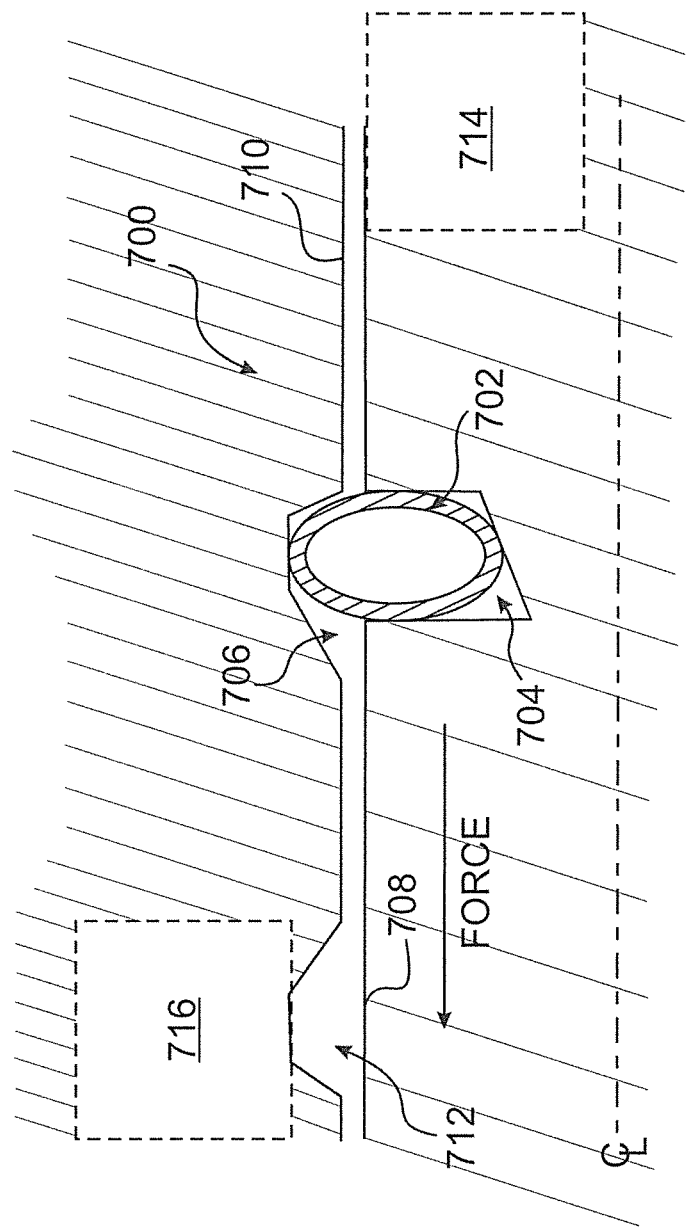
FIG. 9 is a side cross-sectional view of a latch device according to another embodiment.

FIG. 9 is a schematic side view of a multi-stage latching device 700 provided in accordance with another aspect of the present disclosure. Like the devices of FIGS. 6-8, the present device has a first latching position (shown in FIG. 9) when the spring 702 is captured between the groove 704 of the first connector component 708 and the first groove 706 of the second connector component 710. The device has a second latching position (not shown) when the spring is captured between the groove 704 and the second groove 712 of the second connector component 710, such as when applying a force in the direction of the arrow shown in FIG. 9. Also as previously discussed, a progressively higher force is required to move the device into the first latching position, then to the second latching position, and then further beyond the second latching position, which is determined, at least in part, by the tapered sidewalls of the first and second grooves 706, 712. In the present embodiment, the first connector component 708, which may be a pin, a cylindrical member, or a shaft, is connected to a first article of manufacture 714 and the second connector component 710 may be part of a second article of manufacture 716 or is attached to the second article of manufacture.

In practice the first and second article of manufactures 714, 716 may embody any number of items, structure or devices that make use of multi-latching capabilities with progressively higher forces, such as a device with serial latching by incorporating two or more latching points that latch at any particular point depending on the applied force on the device. For example, the first article of manufacture 714 may be a main member and the second article of manufacture 716 may be a base member, as discussed above with reference to FIG. 4. In another example, the first article of manufacture may be a window and the second article of manufacture may be a wall frame for retaining the window. The first latching position allows the window to be initially set to the frame and the second latching position allows the window to be more permanently set to the frame. As another example, a door panel on an automobile may incorporate the multi-latching device of the present disclosure, as can a panel on an airplane.

One of ordinary skill in the art will readily recognize that different latching forces can be provided in a latch device according to the disclosure by providing different configurations for groove(s) on a shaft and/or groove(s) on the housing. A deeper groove captures a larger portion of the canted coil spring, hence providing less compression on the spring and lower latching force than a similarly shaped but shallower groove. The inclination of the sidewalls of a groove affects the force required to unlatch the connection between the shaft and the housing. For example, a steeply inclined sidewall provides a greater latching force than a shallower side wall of a similarly shaped groove having the same depth. Thus, each groove of a latch device according to the disclosure can be configured to provide a preferred latching force. Any of the grooves can also be configured to provide a locking connection or a holding connection between the shaft and the housing. Further detail regarding connection of two components with a canted coil spring and the effect of groove shape and spring characteristics on the resulting type of connection is provided in U.S. Pat. Nos. 4,678,210; 5,082,390; 5,411,348; 5,545,842; 6,749,358; 6,835,084; 7,070,455; and 7,195,523, all of which are expressly incorporated herein by reference.

The above description presents the best mode contemplated for the progressive multi-stage release device, in such full, clear, concise, and exact terms as to enable any person skilled in the art to which it pertains to make and use the progressive release device. The progressive release device, however, is susceptible to modifications and alternate constructions from that discussed above that are equivalent. Consequently, the progressive release device is not limited to the particular embodiments disclosed. On the contrary, the disclosure covers all modifications and alternate constructions coming within the spirit and scope of the disclosure as generally expressed by the following claims, which particularly point out and distinctly claim the subject matter of the disclosure. In addition, aspects or features discussed for one embodiment but not another may be understood to be interchangeable or adaptable to the non-discussed embodiment provided the features are compatible.

What is claimed is:

1. A device with multi-stage engagement comprising:
a first component defining a first axis;
a second component defining a second axis connected to the first component with a first canted coil spring captured by a groove located on the second component and a groove located on the first component;
a third component defining a third axis connected to the second component with a second canted coil spring; and
wherein the first, second, and third axes are common to one another and define a common axis, and a force required to release the connection between the second component and the third component is less than a force required to release the connection between the first component and the second component, and wherein the device has two release configurations including:
a first release configuration in which the third component moves relative to the second component and relative to the first component along the common axis; and
a second release configuration following the first release configuration in which movement of the third component causes the second component to move together with the third component but relative to the first component along the common axis.

2. The device of claim 1, wherein the second canted coil spring is captured by a groove located on the second component and a groove located on the third component.

3. The device of claim 1, wherein the groove of the first connector component has a bottom wall and two sidewalls.

4. The device of claim 1, wherein the second component is located inside the first component.

5. The device of claim 1, wherein the third component is slidable relative to the second component and the first component.

6. The device of claim 1, wherein the third component is made from at least two separate parts that are attached to one another.

7. A method of making a device with multi-stage engagement, the method comprising:
releasably connecting a first component defining a first axis to a second component defining a second axis with a first canted coil spring captured by a groove located on the second component and a groove located on the first component, the connection being releasable with a first required force exerted on at least one of the first component or the second component;
releasably connecting the second component to a third component defining a third axis with a second canted coil spring, the connection being releasable with a second required force exerted on at least one of the second component or the third component;
wherein the first, second, and third axes are common to one another and define a common axis, and the second force is less than the first force, and
wherein the device has two release configurations including:
a first release configuration in which the third component moves relative to the second component and relative to the first component along the common axis; and
a second release configuration following the first release configuration in which movement of the third component causes the second component to move together with the third component but relative to the first component along the common axis.

8. The method of claim 7, wherein the first canted coil spring is an axial canted coil spring.

9. The method of claim 7, wherein the second canted coil spring is captured by a groove located on the second component and a groove located on the third component.

10. The method of claim 7, further comprising locking the second component to the third component by loading the second canted coil spring along its major axis.

11. The method of claim 7, further comprising sliding the third component relative to the second component.

12. The method of claim 7, further comprising placing the second component inside the first component.

* * * * *

UNITED STATES PATENT AND TRADEMARK OFFICE
CERTIFICATE OF CORRECTION

PATENT NO.          : 9,004,805 B2
APPLICATION NO.     : 13/304004
DATED               : April 14, 2015
INVENTOR(S)         : Derek Changsrivong et al.

It is certified that error appears in the above-identified patent and that said Letters Patent is hereby corrected as shown below:

On the Title page, in item (57), in column 2, in "Abstract", line 4, delete "mounted" and insert -- a canted --, therefor.

On the Title page, in item (57), in column 2, in "Abstract", line 9, after "higher" delete "a".

In The Specification

In column 3, line 65, delete "embodiment;" and insert -- embodiment. --, therefor.

In column 5, line 5, delete "i.e." and insert -- i.e., --, therefor.

In column 5, line 9, delete "component" and insert -- component 22 --, therefor.

In column 5, line 41, delete "some" and insert -- same --, therefor.

In column 6, line 35, delete "48. i.e." and insert -- 48, i.e., --, therefor.

In column 8, line 19, delete "A1" and insert -- A1, --, therefor.

In column 8, line 62, delete "shaft" and insert -- shaft, --, therefor.

In column 9, line 8, delete "promoting," and insert -- promoting --, therefor.

In column 9, line 28, delete "example" and insert -- example, --, therefor.

In column 9, line 59, delete "of the of the" and insert -- of the --, therefor.

In column 12, line 29, delete "i.e." and insert -- i.e., --, therefor.

In column 12, line 63, delete "no" and insert -- so --, therefor.

Signed and Sealed this
Seventeenth Day of May, 2016

Michelle K. Lee
*Director of the United States Patent and Trademark Office*